US005543301A

United States Patent [19]

Handelsman et al.

[11] Patent Number: 5,543,301

[45] Date of Patent: Aug. 6, 1996

[54] **METHOD OF IDENTIFYING *BACILLUS CEREUS* HAVING BIOCONTROL ACTIVITY**

[75] Inventors: Jo Handelsman, Madison, Wis.; Larry Halverson, Berkeley, Calif.; Eric V. Stabb, Madison, Wis.; Benjamin Lethbridge, Madison, Wis.; Laura Silo, Madison, Wis.

[73] Assignee: Wisconsin Alumni Research Foundation, Madison, Wis.

[21] Appl. No.: 220,404

[22] Filed: Mar. 30, 1994

Related U.S. Application Data

[63] Continuation of Ser. No. 878,800, May 5, 1992, abandoned, which is a continuation-in-part of Ser. No. 758,644, Sep. 12, 1991, abandoned, which is a division of Ser. No. 194,399, May 16, 1988, Pat. No. 5,049,379, which is a continuation-in-part of Ser. No. 77,850, Jul. 22, 1987, abandoned.

[51] Int. Cl.[6] .............................. C12Q 1/04; C12N 1/20

[52] U.S. Cl. ...................... 435/34; 435/252.5; 435/252.1

[58] Field of Search .................................. 435/34, 252.5, 435/834, 252.1

[56] References Cited

U.S. PATENT DOCUMENTS

| | | | |
|---|---|---|---|
| 2,459,317 | 3/1949 | Vesely et al. . | |
| 2,459,318 | 3/1949 | Vesely et al. | 435/252.1 |
| 3,992,528 | 11/1976 | Graham | 424/177 |
| 4,250,170 | 2/1981 | Kawaguchi et al. | 514/61 |
| 4,877,738 | 10/1989 | Handelsman et al. | 435/252.5 |
| 4,878,936 | 11/1989 | Handelsman et al. | 71/7 |
| 5,049,379 | 9/1991 | Handelsman et al. | 424/115 |

FOREIGN PATENT DOCUMENTS

| | | |
|---|---|---|
| 0193608 | 9/1986 | European Pat. Off. . |
| 0304178 | 2/1989 | European Pat. Off. . |
| WO88/00966 | 2/1988 | WIPO . |

OTHER PUBLICATIONS

Buchanan, R. E. and N. E. Gibbons, *Bergey's Manual of Determinative Bacteriology,* 8th Ed., pp. 532–535 (1974).

Oki et al., *J. Antibiot.* (*Tokyo*), 42, 1749–55.

Ibid., 1756–1774, 1980.

Tschen et al., *Proc Natl. Sci. Counc. Repub. China Part B Life Sci.* 13, 258–261, 1989.

Goto et al., Tetrachedron Lett. 23 1271, 1982.

Hutchins, A. S., "An In Vitro Inhibition of Root Rot Pathogens *Phellinus weiri, Armullariella mellea, Fomes annosus,* and *Phytophithora Cinnamomi* by a Newly Isolated Bacillus sp.," Microb. Ecol. 6(3):252–259 (1980).

Wakayama, et al., "Mycocerein, A Novel Antifungal Peptide Antibiotic Produced by *Bacillus cereus,*" Antimicrobial Agents Cemotherapy, 26:6:939–940 (1986).

Kamicker, B. J. and W. Brill, "Identification of Bradyrhizobium Japonicum Nodule Isolates from Wisconsin Soybean Farms," *Applied Environmental**.

Gurusiddaiah, S. et al., "Characterization of an Antibiotic Produced by a Strain of Pseudomonas Fluorescens Inhibatory to Gaeumannomyces Graminisvar. *tritici* and Pythium spp.,"*Antimicrobial Agents and Chemotherapy* 29:3:488–495 (1986).

Misagahi, I. J., et al., "Fungistatic Activity of Water–Soluble Flourescent Pigments of Flourescent Pseudomonads,"*Phytopathology* 72:1:33–35 (1982).

Howell, C. R. and R. D. Stipanovic, "Suppression of *Pythium ultimum*–Induced Damping–Off of Cotton Seedlings by *Pseudomonas fluorescens* and Its Antibiotic, Pyoluteorin,"*Phytopathology* 70:8:712–715 35 (1982).

Howell, D. R., et al., "Control of *Rhrizoctonia solani* on Cotton Seedlings with *Pseudomonas fluorescens* and With Antibiotic Produced by the Bacterium,"*.

*Phytopathology* 69:5:480–482 (1979).

Pazinski, J. and B. G. Rolfe, "Influence of *Azospirillum Strains* on the Nodulation of Clovers by Rhizobium Strains, "*Applied and Environmental Microbiology* 49:4:984–514.

Yahalom, E., et al., "*Azospirillum* Effects on Susceptibility to *Rhizobium* Nodulation and on Nitrogen Fixation of Several Forage Legumes,"*Can. J. Microbiol.* 33:510–514.

Handelsman, "Abstract" on the Isolation of *Bacillus cereus* presented at meeting on or after Jul. 26, 1986.

Handelsman, et al., "Zoospore Lysis in biocontrol of *Phytophthora megasperma* by *Bacillus cereus* U. W. 85" Dept. of Plant Pathology, University of Wisconsin, Madison, WI 53706 (Published Aug. 1987).

Handelsman, J. et al., "Biological Control of Damping–Off of Alfalfa Seedlings With *Bacillus cereus* UW85,"*Applied and Environmental Microbiology* 56:3:713–718 (Mar. 1990).

Halverson, L. J. and J. Handelsman, "Enhancement of Soy Bean Nodulation by *Bacillus ceres* UW85 in the Field and a Growth Chamber,"*Applied and Environmental Microbiology* 57:9:2767–2770 (Sep. 1991).

Halverson, L. J. and J. Handelsman, "Stability of Antibiotic–Resistance Markers in *Bacillus cereus* UW85,"*The Rhizosphere and Plant Growth,* 107 (D. L. Keister and P. B. Cregan Eds., Kluwer Academic Publishers (1991).

Goodman, R. M. and J. Handesman, "Concerted Use of Transgenes and a Biocontrol Agent in Suppression of Diseases in Plants," Poster presented at Midwest Plant Biotechnology Consortium, Indianapolis, IN, Nov. 13–14, 1991 (draft).

Handelsman, J., et al., "Microassay for Biological and Chemical Control of Infection of Tobacco by *Phytophthora parasitica* var. *nicotianae* ,"*Current Microbiology* 22:317–319 (1991).

Campbell, R. and A. Clor, "Soil Moisture Affects the Interaction Between *Gaeumannomyces graminis* var. *tritici* and Antagonistic Bacteria"*Soil Biol. Biochem.* 17:4:441–446 (1985)

(List continued on next page.)

*Primary Examiner*—Irene Marx

*Attorney, Agent, or Firm*—Quarles & Brady

[57] ABSTRACT

The invention includes a substantially pure preparation of *Bacillus cereus* antibiotic. The invention further includes a seed inoculum for application to seeds to be protected from damping off and root rot including a non-interfering carrier and an effective quantity of *Bacillus cereus* antibiotic, and a method for protecting plants in a growing medium from damping off and root rot including the step of placing in the growing medium in the immediate vicinity of the plant to be protected an effective quantity of *Bacillus cereus* antibiotic.

3 Claims, No Drawings

OTHER PUBLICATIONS

Phipps, P. M. "Evaluation of Biological Agents for Control of Sclerotinia Blight of Peanuts,"B and C Test 7 (1992).

Miller, S. A., "Cytological and Biochemical Factors Involved in the Susceptible, Host Resistant and Non–host Resistant Interactions of Alfalfa," Ph.D. Theses, University of Wisconsin, p. 48 (1982).

METHOD OF IDENTIFYING *BACILLUS CEREUS* HAVING BIOCONTROL ACTIVITY

CROSS-REFERENCE TO RELATED APPLICATIONS

This application is a continuation of application Ser. No. 07/878,800, filed May 5, 1992, now abandoned; which is a continuation-in-part of Ser. No. 07/758,644 filed Sep. 12, 1991 now abandoned, which was a divisional of Ser. No. 07/194,399 filed May 16, 1988, now U.S. Pat. No. 5,049, 379, which was a continuation-in-part of Ser. No. 077,850 filed Jul. 22, 1987, now abandoned.

TECHNICAL FIELD

The present invention relates to combatting damping off and root rot in plants and, in particular, to doing so by means of application of a fungicide.

BACKGROUND OF ART

Certain plants, of which alfalfa, soybeans, and common beans are examples, suffer from disease conditions called "damping off" and "root rot." The symptoms of damping off include the desiccation and subsequent death of seedlings soon after germination. Root rot symptoms include chlorosis and wilt of leaves and yellow to brown lesions with diffuse margins on roots and stems. The lesions can eventually lead to girdling and subsequent root decay resulting in decreased robustness in the plant or even in death. Often plants suffering from root rot begin by showing such symptoms, which may be mistaken as symptoms of drought and starvation. Such plants may be more vulnerable than healthy plants to attack by other pathogens, which are then mistaken as the cause of the death of the plants.

Damping off and root rot are merely two different sets of symptoms caused by infection of the plant by the same fungi and, in particular, by members of the Phytophthora, Pythium, Aphanomyces, Rhizoctonia, and Fusarium genera. Thus, *Phytophthora megasperma* f. sp. medicaginis (hereinafter "Pmm") causes both damping off and root rot in alfalfa when soils are wet in most parts of the world where alfalfa is grown, and *Phytophthora megasperma* f. sp. *glycinea* has been shown to cause root rot in soybeans under wet growing conditions. However, fungi from among the other genera listed also are believed to attack alfalfa and soybeans. Root rot in common beans is believed caused by a complex of fungi including members of more than one of the genera referred to.

In general, control of damping off and root rot has been attempted by breeding for resistant plants. However, completely resistant cultivars have not been developed such that damping off and root rot remain major causes of crop loss. This is especially true under chronically wet growing conditions or when the same crop is planted repeatedly in the same fields. Certain fungicides such as metalaxyl partially control root rot. However, such fungicides are fairly expensive. For some crops, such as alfalfa, their use is not economically feasible. Also, resistance of the fungi to the fungicides can develop rapidly.

"Biological control" is defined as pathogen control by the use of a second organism. Mechanisms of biological control are diverse. For example, certain enteric bacteria have been examined for their usefulness in biological control of root rot in alfalfa. It is believed that control is obtained by competition between the enteric bacteria and the fungi for space on the surface of the alfalfa roots. In contrast, a toxin produced by one species of bacteria may be used to control another species of bacteria that appears as a pathogen. Bacterially produced antibiotics are an example of such toxins. The toxin can be isolated from the species producing it and administered directly, as is the common procedure with penicillin, or the species itself may be administered under appropriate circumstances to produce the toxin in situ. Once identified, such toxins produced by soil-dwelling bacteria may have utility in diverse other areas as antifungal or antibiotic agents.

BRIEF SUMMARY OF THE INVENTION

The protecting toxin of the invention is a *Bacillus cereus* antibiotic, designated here zwittermicin, as characterized and identified below.

The seed inoculum of the invention for application to seeds to be protected from damping off includes a non-interfering carrier and an effective quantity of *Bacillus cereus* antibiotic.

The present invention is also directed toward characterizing the novel antibiotic, zwittermicin, and toward providing multiple sources for the antibiotic.

The present invention is also directed to a novel method for identifying new strains of bacterial strains useful for biocontrol, which strains also produce the antibiotic.

Other objects, features and advantages of the present invention will become apparent from the following specification.

DETAILED DESCRIPTION OF THE PREFERRED EMBODIMENT

An original bacterial strain was isolated from soil that exerts biological control over species of fungi responsible for damping off and root rot in plants. The strain has been deposited in the American Type Culture Collection, given the designation ATCC 53522, and shall hereinafter be referred to as "ATCC 53522." It has further been discovered that certain mutants of ATCC 53522 also provide biological control comparable to that provided by ATCC 53522. These bacteria have been obtained in substantially pure cultures. A "substantially pure" culture shall be deemed a culture of a bacteria containing no other bacterial species in quantities sufficient to interfere with replication of the culture. In addition, it has been discovered that the biological control is exerted by means of a toxin produced by the disclosed bacterial strains.

ATCC 53522 and what are defined below as its "protecting" mutants, together with toxins produced thereby, inocula containing the bacteria or their toxins, and methods for protecting plants from damping off and root rot that utilize the bacteria or their toxins are the subject of a co-pending patent application. Now a particular molecule, a toxin found in supernatant fluid and other bacteria-free fluid and culture medium removed from a culture of ATCC 53522 or of its protecting mutants, has been found to be a "protecting toxin," as that term is defined below. This toxin has been so characterized as to be identifiable independent of its source in cultures of ATCC 53522, or its protecting mutants and, shall be referred to herein both as "*Bacillus cereus* antibiotic" and by the coined term "zwittermicin." Another fraction from the supernatant fluid from a culture of *B. cereus* ATCC 53522 has been found biologically active, having a zoolysin capability to Pmm zoospores, but, as revealed below, this zoolysin active fraction does not have the antifungal activity of the antibiotic. *Bacillus cereus* antibiotic has been found to be a highly water soluble molecule of about 396 daltons in size. The molecule is a zwitterion, that is contains both acid and base groups, includes two amino groups, and is a poly-alcohol.

The method by which the biological control referred to in the preceding paragraph may be verified to exist is the "plant protection assay" detailed below. "Biological control" of fungi causing damping off and root rot shall be deemed to exist if, when an effective quantity of ATCC 53522, its mutants that exhibit biological control, the anti-fungal toxin produced by them, *Bacillus cereus* antibiotic, or any other compound or molecule is placed in the soil or other growing medium in the immediate vicinity of the plant to be protected, a statistically significant reduction in the symptoms of damping off or root rot occurs. An "effective quantity" to combat damping off and root rot shall be that quantity sufficient to result in such a visibly significant reduction of symptoms. Clearly, if no quantity of a bacteria or any toxin or other compound is an effective quantity as so defined, that bacteria, toxin, or compound is not capable of exerting biological control over the fungi causing damping off and root rot.

ATCC 53522 and those of its mutants capable of exerting such biological control shall sometimes be referred to collectively as "protecting" bacteria. *Bacillus cereus* antibiotic and other toxins capable of exerting such biological control shall sometimes be referred to as "protecting" compounds or toxins. Plants, including seeds, seedlings, and mature plants, treated with such an effective quantity of protecting bacteria, their toxins, or *Bacillus cereus* antibiotic shall be referred to as "protected" from root rot or damping off.

ATCC 53522 was one of some 500 bacteria strains isolated from alfalfa roots and accompanying soil obtained from fields at the University of Wisconsin Experimental Farms at Arlington and Marshfield, Wis., and from two private farms at Verona and Cross Plains, Wis. The roots were cut into 1 cm segments, and each segment was placed in 10 ml of sterile, distilled water. The root segment and water then were sonicated at 20% maximum power with a Vibra-Cell 250 watt sonicator obtained from Sonics and Materials, Inc., Danbury, Conn. Sonication was continued for 15 seconds. The sonicated mixture then was diluted in sterile, distilled water, and the dilutions were placed on trypticase soy agar (hereinafter referred to as "TSA") in petri plates to form dilution plates. TSA contains 30 g/l trypticase soy broth (hereinafter referred to as "TSB") obtained from BBL Microbiology Systems, Inc., Cockeysville, Md., and 15 g/l agar. TSA and TSB are conventional bacterial culture media well known to those skilled in the art.

The dilution plates were incubated at 28° C. for two days. For each root sample, bacterial colonies were selected from the dilution plate that had the highest number of distinguishable colonies. One colony of each visually distinguishable morphology on the plate was sampled with a sterile loop and was plated on a new TSA culture plate to allow the development of colonies in plates free from contamination by other bacteria. After two days incubation at 28° C., a single colony was selected from the resulting bacterial growth and was used to inoculate a TSA slant. The resulting slant cultures were stored at 4° C. until they were screened by the plant protection assay disclosed below.

Five hundred different slant cultures were obtained by this method. As a consequence of the isolation procedure just reviewed, it was extremely unlikely that any of these 500 cultures were immediate siblings. However, fewer than 500 separate bacterial species were isolated. For example, a number of different cultures were obtained of bacteria whose colonies had the appearance of *Bacillus cereus*, including the culture identified above as ATCC 53522. However, each of these cultures had been obtained from a different root segment, and the root segments themselves were obtained from fields from four different geographical locations. Consequently, the chances that a single strain was present in more than one slant culture are very small. This fact is confirmed by the appearance of ATCC 53522 in only one of the 500 cultures.

Each of the cultured isolates that were obtained by the procedure just described were screened for their ability to protect alfalfa seedlings from damping off caused by Pmm. Initial screening was performed on the cultivar Iroquois, which is known to be vulnerable to Pmm. One gram of Iroquois alfalfa seeds was soaked in 18M sulfuric acid for 10 minutes. The seeds were then washed in 2 l of sterile distilled water and were placed in 10 ml of sterile water and shaken at 28° C. for 24 hours. Next the seed coats were removed manually with forceps, and the seedlings were planted in test tubes containing 5 ml sterile, moist vermiculite. Three seedlings were planted in each test tube. Two days after the seedlings were planted, each test tube was inoculated with 0.3 ml of a two-day-old culture of the bacterial isolate to be tested. These cultures had been grown to saturation in TSB and had sporulated. Then each tube immediately was inoculated with 10 zoospores of Pmm.

The Pmm zoospores had been produced by the method of S. A. Miller (1982) "Cytological and Biochemical Factors Involved in the Susceptible, Host Resistant and Non-host Resistant Interactions of Alfalfa with *Phytophthora megasperma*," Ph.D. thesis, University of Wisconsin. By this method, a sample of a colony of Pmm was transferred to an agar media on which it could grow. Conventional V8 media was used, consisting of 200 ml V8 vegetable juice, 2.5g $CaCO_3$, and 15 g agar in 800 ml water. However, any agar media such as conventional tomato juice agar or carrot agar encouraging the growth of the fungus would be sufficient. The sample of the fungus colony was incubated at 24° C. for 4 days and then at 28° C. for an additional 3 days. A growing colony of Pmm developed. The agar around the colony was excised to leave a section of undisturbed agar with the growing fungus on it surrounded by a "moat" formed by the excision of agar. This moat was filled with sterile water to the level of the agar that had not been excised. The plate was incubated at 16° C. for one hour, whereupon the water was replaced, and the plate was incubated at 16° C. for an additional 5 hours. Zoospores were released from the fungus into the water of the moat. The concentration of zoospores in the water was measured with a hemacytometer, and a sample of the water was diluted with additional sterile water at 16° C. to reach a final concentration of zoospores of 104/ml.

After addition of the zoospores, the test tubes containing the plants were incubated at 24° C. with a 12 hour photoperiod for 5 days, at which time the plants were evaluated for symptoms of damping off. Using Pmm and cultivar Iroquois, all control plants consistently were dead. Thus, the fact that a plant survived at all was evidence of biological control exerted by the bacterial isolate used. All bacteria that demonstrated that minimal amount of effectiveness for biological control were retested by this same method to verify the consistency of such control. The screening procedure just described constitutes a particular example of the plant protection assay described more generally below.

Of the 500 isolates from the 4 sites in Wisconsin referred to above, only ATCC 53522 strain was identified as having the ability consistently to exert biological control of Pmm in Iroquois alfalfa, as evidenced by at least 20 separate experiments. The level of control was such that alfalfa seedlings subjected to such control under the conditions of the screening procedure were visually indistinguishable from alfalfa seedlings that had never been exposed to Pmm. ATCC 53522 has been classified as *Bacillus cereus*, based on physiological tests, its colony morphology, and its spore size, shape, and position. Thus, ATCC 53522 produces acetoin, forms an acid from glucose broth, hydrolyzes starch, and grows in anaerobic agar. These characteristics, together with colony morphology, and spores size, shape, and position observed in ATCC 53522 are cited as distinctively characteristic of *Bacillus cereus* by R. E. Buchanan and N. E. Gibons, co-editors (1974), *Bergey's Manual of Determinative Bacteriology*, 8th Edition, pp. 532–535.

*Bacillus cereus* is a not uncommon bacterium in field soils. However, strains of *Bacillus cereus* demonstrating antifungal activity are almost unheard of. The inventors originally tested two known strains of *Bacillus cereus* obtained from entirely separate sources and found neither of them to exhibit the anti-fungal properties of ATCC 53522. Subsequently, as discussed further below, a method was derived to screen other field isolates for antibiotic production, and other such strains can now readily be found. In the original screening, however, of the 500 root-associated bacteria reviewed in the isolation process, many were probably *Bacillus cereus* and, in fact, many of them had the same colony morphology at ATCC 53522, but none of these other strains exhibited the antifungal qualities of ATCC 53522. S. Wakayama, et al. (1984)., *Antimicrob. Agents Chemother.,* 26, 939–940, describe antifungal activity in a strain of *Bacillus cereus.* However, most of the antifungal antibiotics are made by *Bacillus subtilis,* which is easily distinguishable from ATCC 53522. The antifungal toxin produced by ATCC 53522 differs from that of the reported strain of *Bacillus cereus* referred to in that the toxin is of lower molecular weight and has different solubility properties. In addition, ATCC 53522 differs from the reported *Bacillus cereus* strain in that it grows anaerobically whereas the reported strain does not. Consequently, it is clear that the two *Bacillus cereus* strains are not the same and that their toxins are not the same.

The following is a disclosure of the plant protection assay whereby a test material such as a bacteria, a toxin, or the like, may be tested for its ability to exert biological control over a fungus capable of causing the symptoms of damping off or root rot. The seed of the plant to be protected is planted in a planting medium in the presence of damping off or root rot causing fungi. The planting medium may be a damp soil containing such fungi, vermiculite in water with the fungi present either in the vermiculite and water or in or on the seed, or any other planting medium in which the seed will grow and the fungi may freely develop. The bacteria, toxin, or other test material is placed at least in the immediate vicinity of the seed. Such placement shall be understood to be in the "immediate vicinity" of the seed if any soluble test material or any soluble exudate of a bacteria being tested will be in actual contact with the seed as it germinates.

Preferably the seed is coated with the test material, and when the test material is so used with respect to a seed, it shall be referred to hereinafter as a "seed inoculum." The process of coating seed with a seed inoculum is generally well known to those skilled in the art, and any conventional method that does not require conditions sufficiently harsh to kill bacteria or destroy toxins or other materials included in the seed inoculum is adequate. An easy and preferred method is to suspend or dissolve the test material in a 1.5% aqueous solution of methyl cellulose. For convenience, it will be presumed hereinafter that the seed inoculum is a bacteria suspended in the methyl cellulose, although a dissolvable material such as a bacterial toxin may be handled in the same manner. The plant seed to be protected is added to the suspension and is mixed vigorously with it to coat the surface of the seed with the suspension. The seed may then be dried aseptically, preferably by being placed within a laminar flow hood on a sterile surface such as a sterile petri plate. The result is a dry, seed inoculum-coated seed. When the coated geed is planted in the planting medium, the test material accompanies it to reside in the immediate vicinity of the geed.

After a time sufficient for seedling growth and the expression of the symptoms of damping off, seedlings developing from the planted seed may be evaluated for visual evidence of protection, when compared to controls. In strains of alfalfa, soybeans, and snap beans known to be vulnerable to damping off, 2 weeks of growing time in a growth chamber at 24° C. with a 12 hour photoperiod was found to be a period sufficient for the expression of symptoms of damping off when seedlings were being grown in test tubes containing roughly 10 zoospores of Pmm or comparable, damping off-causing fungi. Protected seeds developed into seedlings visually indistinguishable from uninfected seeds while control seedlings developing from unprotected seeds were killed or, in the case of snap beans, exhibited brown lesions on roots and stems, stunted roots, rotted roots, and other visually apparent symptoms of root rot.

Protecting mutants of ATCC 53522 include both naturally occurring and artificially induced mutants. For example, ATCC 53522 is generally sensitive to the antibiotics rifampicin and neomycin. However, naturally occurring mutants of ATCC 53522 were isolated that exhibited resistance to one or the other of these antibiotics. Certain of these mutants, as well as one naturally occurring mutant distinguishable from the parent ATCC 53522 strain by the appearance of its colonies, are discussed in the Examples below and were found to protect alfalfa plants in the plant protection assay. Other mutants of ATCC 53522 were artificially induced by subjecting ATCC 53522 to the mutagen N-methyl-nitrogoguanidine in conventional ways, as is discussed in the Examples below. Most of these induced mutants also were found to protect alfalfa plants in the plant protection assay.

As has been disclosed above, it has been further discovered that an active anti-root rot toxin, identified herein as *B. cereus* antibiotic, or zwittermicin, is produced by ATCC 53522 and those of its mutants that are characterized by their abilities to protect plants from root rot in the plant protection assay. *Bacillus cereus* antibiotic may be collected from growth media in which the bacteria have been cultured and has been prepared in a substantially pure form. A preparation of *Bacillus cereus* antibiotic shall be deemed "substantially pure" if it is sufficiently free of interfering substances as to be able to be active to inhibit root rot by Pmm. *Bacillus cereus* antibiotic is effective to protect plants from damping off and root rot even when separated from the bacteria producing it and applied to seed and to seedlings that have been placed in a planting medium containing root rot causing fungi. As is discussed below, the effectiveness of the application of *Bacillus cereus* antibiotic is demonstrable by the plant protection assay, with the antibiotic being substituted for a protecting bacteria. Thus, the invention includes *Bacillus cereus*, antibiotic and a seed inoculum containing effective quantities of *Bacillus cereus* antibiotic.

As has been disclosed above, *Bacillus cereus* antibiotic may be isolated from ATCC 53522 and its protecting mutants by filtering the bacteria from the culture media in which they have been grown to a sporulated culture. Other conventional purification and concentration steps may then be undertaken as may be considered convenient or desirable, so long as the toxin remains active, as may be demonstrated by the plant protection assay.

The chemical formula and structure of the plant protective *Bacillus cereus* antibiotic zwittermicin are not fully known, despite having been the subject of considerable study. The molecular weight of the molecule identified as *Bacillus cereus* antibiotic was originally thought to be between 500 and 1,000 daltons. Subsequent measurement of the molecular weight of purified antibiotic by mass spectroscopy revealed a molecular weight of about 396 daltons. The zwittermicin antibiotic is soluble in methanol and insoluble in acetone, chloroform, and ethyl acetate. The antibiotic binds both to anion and cation exchange columns at the appropriate pHs and is a zwitterion, containing both acidic and basic groups. It is stable for at least ten minutes when heated as high as 80° C. at pH 7.0, but it becomes inactive upon heating for as little as ten minutes to 80° C. at either pH 2.0 or pH 10.0. *Bacillus cereus* antibiotic is also stable for at least three months at 4° C. and for at least two weeks at 25° C. In many repeated experiments, the antibiotic has been tested for its various protecting abilities by the plant protection assay. Tests have revealed that the zoolysin activity of *Bacillus cereus* is not associated with the *B. cereus* antibiotic referred to here as zwittermicin. The antibiotic alone has proven a useful inhibitor of Phytopthora and Pythium species as well as other fungal species. In addition, the toxin also inhibits growth of some bacteria, such as *Erwinia herbicola,* several Pseudomonas species, and some *E. coli* strains.

Despite repeated efforts an unambiguous chemical structure for the zwittermicin molecule has not been yet obtained. However, sufficient data has been generated in order to tentatively specify many characteristics of the *Bacillus cereus* antibiotic. The antibiotic appears to have a backbone of a linear chain of six carbons. The molecule is a polar 6 carbon diamino polyol with the 5 position deoxy and two unidentified substituents. It is also apparent that the amino groups are required for the biological activity. The unknown substituents may be two ethane or ethylene groups, which may or may not be connected to the backbone structure by ester or phosphodiester linkage. It is not certain if the two hydroxyl groups are appended to the backbone or to the ethyl side chains.

Other observations about the character of the molecule are possible. The zwittermicin molecule stains positively by ninhydrin. The molecule chars on paper when heated to 100° C. for twenty minutes. The molecule stains white with silver nitrate against a dark brown background. In staining by tetrazolium, a test for reducing sugars, the molecule tests negatively. Tentative results of elson morgan staining for amino sugars is also negative. If subjected to mobility measurement by paper electrophoresis, comparing relative mobility to the dye stuff standard Orange G, at pH 9.2 the molecule has a relative mobility of 0.3 and at pH 1.7 the molecule has a mobility of −1.042. This compares with a comparable mobility at pH 1.7 of −0.644 for trehalosamine and −0.915 for glucosamine. The relative mobility compared to solvent front (propanol:acetic acid: water; 12:3:5) is 0.29. If run in butanol:acetic acid: water, the $R_F$ is 0.1.

As described below, it is now possible to isolate the zwittermicin antibiotic from a variety of *Bacillus cereus* strains which can be characterized by the assay method described below. Using any of these strains, it is possible to purify from the culture of such strains the antibiotic. The culture media from the bacterial culture, including the antibiotic, is subjected to a CM Sephadex cation exchange chromatography column at pH 7.0. The bound material is eluted from the column at a pH over 9.0. To further purify the material eluted from the column, fractions can be pooled and then subjected to high voltage paper electrophoresis at pH 1.7 or 9.2, looking for the mobility described above. The zwittermicin can be detected by staining with silver nitrate or ninhydrin, or eluted and tested for biological activity. Alternatively, the fractions can be applied to thin layer chromatography plates that are developed in propanol:acetic acid:water (12:3:5). The plate may then be stained with ninhydrin which will reveal a single ninhydrin-positive spot that comigrates with the antibiotic activity.

In preparing quantities of the antibiotic, cultures of the antibiotic-producing bacteria may be centrifuged to remove spores and the supernatant adjusted to a pH of 7.0 with concentrated hydrochloric acid. The neutralized preparation can be applied to the CM Sephadex cation exchange column in the ammonia form. The antibiotic can be eluted with 0.1M ammonia and can be further purified by high voltage paper electrophoresis first at pH 9.2 then at pH 1.7. The spots on the paper can be assayed by biological assay for Erwinia inhibition, as described below, for growth inhibition. Active fractions may be dried and resuspended in water. In this fashion useful quantities of the antibiotic can be, and have been, readily created.

An unexpected discovery has also established that the zwittermicin antibiotic is produced by a number of strains of bacteria, most of which of which are believed also to be *Bacillus cereus.* The surprising discovery was initiated by the discovery that a phage, previously in lysogenic form, could be isolated from the original bacterial strain ATCC 53522. The phage has been designated here P7. A culture of the strain ATCC 53522 was grown in tryptic soy broth with vigorous agitation. During the log-phase growth of the bacterial culture, mitomycin C was added to a final concentration of 1 microgram per milliliter. The culture lysed 8 to 9 hours after addition of the mitomycin C, and a phage was isolated from the remaining culture by plating it on a lawn of ATCC 53522 bacteria grown in soft agar (0.4%). Individual plaques were picked and replated again on the ATCC 53522 bacteria. The phage has been, and may continually, be propagated by plating sufficient lysate with the ATCC 53522 bacteria on a soft agar overlay to result in clearing of the overlay. The overlay may be scraped from the plate, the agar removed by centrifugation, and the supernatant stored for future use, the supernatant containing the phage.

The discovery of the phage P7 was unexpected. In investigating the properties of the phage P7, it was decided to test various isolates of new root-associated and soil-associated bacteria for their sensitivity to infection by this phage. In that process, initial tests were conducted of the same bacteria for biocontrol activity. Surprisingly, it was found that there was a correlation between sensitivity to phage P7 infection and the ability of the bacteria to exhibit biocontrol activity in laboratory tests for such activity. In fact, in relatively limited sampling, 5 different strains of *Bacillus cereus* were isolated from legume roots which were sensitive to infection by the phage P7, produced the zwittermicin antibiotic as determined by ninhydrin staining and also exhibited biocontrol activity in an Erwinia bacterial growth inhibition laboratory assay developed, and described below. Nevertheless, the new strains which produce the antibiotic are distinguishable among themselves, and from strain ATCC 53522. Hence, by utilizing the combination of three assays, it is possible to isolate a whole new class of strains of biocontrol bacteria having activity similar to the plant protecting activity of ATCC 53522 described herein. In general the phage assays may be the most convenient while the Erwinia biocontrol assay seems to correlate well with biocontrol activity.

The laboratory assay for biocontrol activity was performed using the bacteria *Erwinia herbicola.* While not all strains of Erwinia are sensitive to the antibiotic, it is believed that many strains are sensitive to it. This assay for antibiotic production can be performed with any sensitive strain. Strains of Erwinia can be tested for zwittermicin sensitivity using filtrates from media of ATCC 53522 cultures.

The inoculum of the invention for the protection of plants from damping off and root rot includes a quantity of *Bacillus cereus* antibiotic in a carrier harmless to the plants to be treated and non-interfering with the effects of the *Bacillus cereus* antibiotic. Such carriers shall be referred to as "non-interfering carriers." Examples of preferred non-interfering carriers are water and a 1.5% methyl cellulose aqueous solution.

The examples below provide specific data and information relating to the invention as broadly disclosed herein, although the invention is not to be understood as limited in any way to the terms and the scope of the examples.

EXAMPLE 1

Plant Protection Assay of ATCC 53522 Using Alfalfa

The screening procedure disclosed above was repeated as an application of the plant protection assay to test the protective ability of ATCC 53522 with alfalfa. The cultivar of alfalfa used was Iroquois. The fungus used was Pmm. One gram of seeds was soaked in 18M sulfuric acid for ten minutes, washed in 2 1 of sterile distilled water, placed in 10 ml of sterile distilled water, and shaken at 28° C. for 24 hours. Thereafter, the seed coats were removed with forceps, and the seedlings were planted in test tubes containing 5ml of moist vermiculite. Three seedlings were planted in each test tube. After two days, each test tube was inoculated with 0.3 ml of a two day old culture of ATCC 53522 that had been grown in TSB to saturation. Thereafter, each tube was inoculated with $10^3$ zoospores of Pmm. The plants then were incubated at 24° C. with a 12 hour photo period for 5 days, whereupon the plants were evaluated for viability. All of the control seedlings were dead. The seedlings that had been treated with ATCC 53522 had the appearance of normal seedlings that had not been exposed to Pmm.

EXAMPLE 2

Plant Protection Assay of ATCC 53522 with Soybeans

The procedure of Example 1 was repeated with soybeans of the variety McCall substituted for the alfalfa seeds and zoospores of *Phytophthora megasperma* f. sp. *glycinea* substituted for the zoospores of Pmm. Instead of being planted in test tubes, the soybean seeds were planted in 10 ml plastic cones having holes in the bottom, and the cones were placed in a pan of water. The seedlings were examined for protection two weeks after inoculation with the zoospores. Ten out of 10 controlled seedlings were killed by the fungus. All of the seedlings that had been treated with ATCC 53522 survived with healthy, white roots.

EXAMPLE 3

Plant Protection Assay of ATCC 53522 with Snap Beans

The procedure of Example 2 was repeated with snap beans of the variety Early Gallatin, and the fungi used were naturally occurring fungi present in a soil sample from the University of Wisconsin Experimental Station at Hancock, Wis. All of the control seedlings developed root rot symptoms within two weeks, including brown lesions on roots and stems, stunted roots, and rotted roots. The seedlings that had been treated with ATCC 53522 developed reduced root rot symptoms in the same period of time.

EXAMPLE 4

Field Test of ATCC 53522

Alfalfa seeds of the cultivar Iroquois were mixed in a suspension of ATCC 53522 in 1.5% methyl cellulose. The bacteria had been cultured on a TSA plate that had been incubated at 30° C. for two days, by which time the culture had sporulated. The culture then was scraped into 3 ml of the 1.5% methyl cellulose solution to provide the suspension of bacteria. One gram of alfalfa seeds was added to this suspension and was mixed thoroughly therewith. The seed then was spread on sterile petri plates and dried overnight in a laminar flow hood. The coated seeds were planted in circular plots 0.3 m in diameter at Marshfield, Wis. Owing to dry growing conditions, both emergence of plants and evidence of Pmm damping off were poor. Nevertheless, emergence in a control, untreated plot was 18% whereas in the plot planted with bacterium-treated seed, emergence was 30%. An additional plot was planted with seed that had been coated with a fungicide, metalaxyl, a conventional control agent for damping off. In that plot, emergence was 29%. Thus, it is apparent that ATCC 53522 can protect alfalfa in the field as effectively as does metalaxyl. Furthermore, symptoms of root rot became apparent in the control plot having untreated seeds as the growing season proceeded. No symptoms of root rot appeared in the plot planted with the seeds coated with ATCC 53522.

EXAMPLE 5

Plant Protection Assay. of ATCC 53522 Toxin

The method of Example 1 was repeated with ATCC 53522 being replaced with a filtrate of a culture of that bacterium. The filtrate was prepared by centrifuging a two day old, saturated broth culture at 10,000 g for ten minutes and then filtering the resulting supernatant twice through 0.45 μ filters. The filtrate was stored at −20° C. before being applied in the plant protection assay identically to the way the bacteria had been applied in the experiment reported as Example 1. The protective effect observed in treated alfalfa seedlings versus untreated seedlings was identical to that reported in Example 1. The filtrate used in this example contained *Bacillus cereus* antibiotic.

EXAMPLE 6

Spontaneous Mutants of ATCC 53522

Spontaneously developing antibiotic resistant mutants of ATCC 53522 were isolated by plating a culture derived from a colony of ATCC 53522 on media containing an antibiotic to which ATCC 53522 normally is sensitive. Several resistant colonies developed. They were each sampled with a sterile toothpick and replated on the antibiotic-containing media. The mutants were then tested in the plant protection assay by the procedure described in Example 1. Five mutants were developed that were resistant to rifampicin. A sixth mutant was developed that was resistant to neomycin. Each of the mutants protected alfalfa plants in the plant protection assay as applied in Example 1 as effectively as did ATCC 53522.

EXAMPLE 7

Induced Mutants of ATCC 53522

A culture of vegetatively growing cells of ATCC 53522 was prepared and diluted to a density of 108 cells/ml. A quantity of this culture was treated by exposure to 1 μg/ml N-methyl-nitrosoguanidine for thirty minutes at room temperature. The cells then were washed with water and dilution plates were prepared on TSA. The treatment with N-methyl-nitrosoguanidine had killed 99% of the bacteria in the original culture. Thus, the remaining viable bacteria each had a high probability of containing at least one mutation. Of 500 such bacteria derived from independent colonies, 490 were able to protect alfalfa plants against Pmm when tested by the method of Example 1.

EXAMPLE 8

The assay procedure of Example 1 was again used to demonstrate that the plant protection activity resides with the *Bacillus cereus* antibiotic by testing filtrate fraction activity with the natural strain and antibiotic deficient mutants. Strain T30 is such an antibiotic deficient mutant derived from *Bacillus cereus* ATCC 53522. The results of this procedure are demonstrated in Table 1 below.

TABLE 1

| | Plant Survival | |
|---|---|---|
| Treatment | Alfalfa | Tobacco |
| None | 0/18 | 0/12 |
| ATCC 53522 | 18/18 | 12/12 |
| ATCC 53522 filtrate | 18/18 | 12/12 |
| ATCC 53522 500–1000 fraction | 18/18 | 12/12 |
| T30 | 0/18 | 2/12 |
| T30 filtrate | 0/18 | 1/12 |
| T30 500–1000 fraction | 0/18 | 0/12 |

This demonstrates that the plant protecting activity is in the *Bacillus cereus* antibiotic independent of the bacteria, and that the activity is absent in antibiotic deficient mutants.

EXAMPLE 9

Isolation of Phage P7

A culture of ATCC 53522 was grown in trypic soy broth with vigorous agitation. During the log-phase growth phase of the bacteria, mitomycin C was added to the media to a final concentration of 1 μg/ml. The bacteria in culture lysed 8 to 9 hours after the addition of the mitomycin C. Phage particles were isolated from the remaining culture by plating aliquots of the culture on a lawn of ATCC 53522 grown in soft agar (0.4%). Individual plaques were then picked and replated again into a similar subculture. The P7 phage has been propagated by plating sufficient lysate on a culture of a ATCC 53522 on a soft agar overlay to result in clearing of the overlay. The overlay has been typically removed from the plate, the agar removed by centrifugation, and the supernatant stored for future use. Later, the supernatant was reinoculated onto culture to continue to propagate and isolate additional phage P7. Samples of the phage P7 have been deposited with the ATCC as Accession No. 75237. The ATCC is located in Rockville, Md. The deposit was made on May 5, 1992.

EXAMPLE 10

Isolation of Other Biocontrol Bacteria

Additional populations of *Bacillus cereus* were recovered from soil or from field-grown soybeans and from alfalfa, soybeans and snapbeans plants grown in field soils in the growth chamber. The samples were dilution plated by sonicated samples of soil, seeds, cotyledons, radicles or 1 to 2 cm root segments taken from 0-1, 0-2, 2-3, 4-5, or 9-10 cm below the crown, or from the last cm of the root. For this purpose, the crown was defined as the part of the plant at the soil-air interface which was marked on each plant as it was removed from the soil. Plant materials placed at either 5 or 10 ml of sterile distilled water, which was then sonicated for 15 seconds at 20% output with a 250 W Vibra-cell sonicator (Sonics and Materials) and then serially diluted in sterile distilled water. Aliquots (0.1 ml) of the dilutions were then plated onto a semi-selective medium. The semi-selective medium (Min IC) medium was used because few non-Bacillus bacteria will grow on it, thereby semi-selecting for the detection of *Bacillus cereus*. The Min IC medium contained, per liter, 2.0 g of $(NH_4)_2SO_4$, 6.0 g of $KH_2PO_4$, 14.0 g of $K_2HPO_4$, 0.2 g of $MgSO_4$-$7H_2O$, 0.25 mg of $MnSO_4$-$H_2O$, 1.0 g of trisodium citrate-2 $H_2O$, 0.1 g of thiamine hydrochloride, 2.0 g of L-glutamic acid, and 5.0 g of acid-hydrolyzed casein (Sigma). After autoclaving, 10 ml of a sterile 50% (wt/vol) glucose solution and 10 ml of sterile $FeCl_3$-$6H_2O$ (4.0 mg/ml) were added. The Min IC medium was also inoculated with 12.5 micrograms/ml polymyxin B-sulfate, 50 μg/ml ampicillin, and 100 μg/ml cycloheximide. The *B. cereus* isolates that were collected from the field were screened on a semi-selective media. Colonies of *B. cereus* were identified by their distinctive colony morphology, i.e., large, flat, wrinkled, cream or orange colored colonies, on the semi-selective medium.

EXAMPLE 11

Screening of Putative Biocontrol Agents

The biocontrol agents isolated in this fashion were then subjected to a selection criteria based on the use of three assays which have been found to have strong correlations with each other, and which are capable of identifying *Bacillus cereus* strains which are capable of biocontrol activity and which produce the zwittermicin toxin. One assay is based on the susceptibility of the candidate strain to infection by the P7 phage. The second test is based on a laboratory biocontrol study using *Erwinia herbicola*. The third study is an actual stain assaying for the production of the zwittermicin toxin itself. All of these assays correlate well, although not perfectly. So far, however, every strain found to be susceptible to P7 has tested positive for Erwinia inhibition and has stained for antibiotic production. The results of these assays, done collectively or singly, may be verified by biocontrol studies on actual plants.

The phage sensitivity selection was done using the following protocol. High titer preparations (in excess of $10^9$ pfu/ml) of phage P7 were prepared either from infected broth cultures or from top agar overlays of *Bacillus cereus* ATCC 53522 as described in the prior example. The cells were removed by centrifugation and the supernatants were filtered (0.2 micron or 0.45 micron filters). The phage preparations were titered and stored in a refrigerator. Separately, cultures of the candidate organisms were grown on 50% trypsin soy agar (TSA). The growth is scraped from the .culture plate, suspended in a small volume of 50% trypsin soy broth (TSB), and added to three milliliters of molten 50% TS top agar (0.4% agar) and spread on a plate of 50% TSA. Drops of the high titer phage stock, approximately 10 microliter in size, were placed on the plate. The plates were incubated overnight at 28° C. If the drop of phage introduced into the culture caused a clear zone, the strain was scored as sensitive to the phage.

The laboratory biocontrol assay for *Erwinia herbicola* inhibition was conducted as follows: The Erwinia culture was grown in 50% TSB with shaking, over night, at 28° C. The Erwinia cells were allowed to settle to the bottom of the tube and the stock of Erwinia was stored in the refrigerator, sometimes for as much as two weeks. The candidate *B. cereus* strain to be tested was grown in 50% TSB, with shaking, at 28° C., for two to three days. Fifteen microliters from the top of the Erwinia stock tube, taken without shaking the tube, was placed in 1 milliliter of sterile water. Eighty-five microliters of the Erwinia dilution was then spread on water agar or 25% trypsin soy agar in a plate. Four holes were cut in the plate with a sterile cork borer. Approximately 100 microliters of the candidate *B. cereus* test culture was added to each of the holes cut in the plate. The zones of inhibition of Erwinia growth around the *B. cereus* cultures were scored in two to three days. Candidates were scored as positive if a zone of inhibition appeared.

To assay for the production of the zwittermicin toxin, cultures of the candidate *B. cereus* cultures were maintained under conditions described above. The cultures were fully sporulated and centrifuged to remove spores. The supernatant was applied to a CM Sephadex cation exchange column in the ammonia form. The column was then washed with buffer (6 mil 10 mM N,N bis (2-hydroxyethyl) 2-amino ethane sulfonic acid, pH 7.0). The bound toxin, if present, was eluted with 10 mM 3-cyclohexylamino propane sulfonic acid, pH 10.4. Fractions were collected, dried in a rotary evaporator and resuspended in water. Resuspended material was spotted onto filter paper and subjected to preparative high voltage paper electrophoresis at pH 1.7 and 300 volts for 15 minutes. Alternatively, fractions from the column were also loaded into several cellulose thin-layer chromatography (TLC) plates that were developed with a propanol:acetic acid:water mixture (12:3:5). TLC plates and filter paper that had been subjected to electrophoresis were stained by dipping in a solution containing 0.25% nihydrin in acetone. The plates of paper were dried and heated at 110° C. until spots were visible. The occurrence of nihydrin staining spots verified production of the antibiotic.

The following Table 2 summarizes the results of assaying the isolated strains. The results demonstrate that the three laboratory tests, P7 susceptibility, Erwinia inhibition, and antibiotic detection correlate nicely with each other and with biocontrol activity. While some strains may fail one of the tests and still have biocontrol capability, so far each strain that has passed one or more assay has exhibited biocontrol activity. Hence these assays, singly or collectively, provide useful laboratory tools to select new biocontrol strains.

TABLE 2

Correlation between Phage Sensitivity, Antibiotic Production and Biocontrol Activity for *B. cereus* isolates

| Strain | P7 Assay | Erwinia Assay | Antibiotic detected | Biocontrol Activity |
|---|---|---|---|---|
| ATCC 53522 | + | + | + | + |
| Laboratory Strains | | | | |
| (7 strains) | – | – | – | nt |
| Soil Isolates | | | | |
| 1 | + | + | + | + |
| 3 other strains | – | – | nt | nt |
| 86 strains | – | nt | nt | nt |
| Soybean Root Isolates | | | | |
| 1 | + | + | + | + |
| 5 other strains | – | – | nt | nt |
| 39 other strains | – | nt | nt | nt |
| Alfalfa Root Isolates | | | | |
| 1 | + | + | + | + |
| 2 | + | + | + | + |
| 3 | + | + | + | + |
| 8 strains | – | + | + | + |
| 1 strain | – | – | – | + |
| 11 strains | – | – | – | – |
| 154 strains | – | – | nt | nt |

nt = not tested

The biocontrol assays were conducted as described in Handelsman et al. , *App. Env. Micro.* 56: 3, pp. 713–718 (1990).

From these results, it is apparent that the production of zwittermicin is a regularly occurring, although not common, phenotype of *Bacillus cereus* strains. Using this practical assay, between 1% and 5% of isolated *B. cereus* strains tested have exhibited antibiotic production. Thus additional strains can readily be isolated by mass isolation and screening using the assays described above. Any such newly isolated strains can be used as a source for the antibiotic and the antibiotic producing strains will exhibit biocontrol activity. While one strain exhibited antibiotic production but was not infected by phage P7, all strains susceptible to P7 have so far exhibited toxin production. In addition, so far the Erwinia bioassay has correlated very well with antibiotic production, and this assay is relatively simple to perform, thereby greatly facilitating identification of other *B. cereus* which produce the antibiotic.

It will be apparent to those skilled in the art that a number of modifications and changes can be made without departing from the spirit and scope of the present invention. Therefore, it is not intended that the invention be limited by the terms of the general disclosure above nor by the Examples but only by the claims, which follow.

What is claimed is:

1. A method of identifying *Bacillus cereus* strains having biocontrol activity comprising the following steps in order:

(a) isolating strains of bacteria from soil or roots of legumes;

(b) selecting for strains having all of the taxonomic characteristics of *Bacillus cereus;*

(c) selecting the *Bacillus cereus* strains obtained in (b) that are susceptible to phage P7, as demonstrated by lysis thereof; and (d) verifying biocontrol activity by identifying the cells obtained in (c) which inhibit the growth of *Erwinia herbicola.*

2. The method of claim 1 further comprising the following step:

(e) identifying the *Bacillus cereus* strains obtained in (d) which produce the antibiotic zwittermicin by assaying therefor.

3. A method of identifying *Bacillus cereus* strains producing zwittermicin antibiotic comprising the following steps in order:

(a) isolating strains of bacteria from soil or roots of legumes;

(b) selecting for strains having all of the taxonomic characteristics of *Bacillus cereus;*

(c) selecting the *Bacillus cereus* strains obtained in (b) that are susceptible to phage P7, as demonstrated by lysis thereof; and (d) selecting the *Bacillus cereus* strains obtained in (c) which produce the antibiotic zwittermicin by assaying therefor.

* * * * *